United States Patent [19]

Tada et al.

[11] Patent Number: 4,615,761
[45] Date of Patent: Oct. 7, 1986

[54] METHOD OF AND APPARATUS FOR DETECTING AN END POINT OF PLASMA TREATMENT

[75] Inventors: Keiji Tada; Takashi Fujii; Gen Marumoto; Kazuhiro Jyouo, all of Kudamatsu; Takahiro Fujisawa, Yanai, all of Japan

[73] Assignees: Hitachi, Ltd.; Hitachi Sanki Eng Co., Ltd., both of Tokyo, Japan

[21] Appl. No.: 712,032

[22] Filed: Mar. 15, 1985

[51] Int. Cl.$^4$ .................. H01L 21/306; B44C 1/22; C03C 15/00; C23F 1/02
[52] U.S. Cl. .................. 156/626; 156/345; 156/643; 156/646; 204/192.33; 204/298
[58] Field of Search .............. 156/345, 643, 646, 626, 156/627; 204/192 E, 298; 118/50.1, 620, 728; 427/38, 39; 356/300, 302, 316, 437

[56] References Cited

U.S. PATENT DOCUMENTS 4,415,402 11/1983 Gelernt et al. ............... 156/626
4,491,499 1/1985 Jerde et al. ............... 156/627 X

FOREIGN PATENT DOCUMENTS 0169241 10/1982 Japan ............... 156/627

Primary Examiner—William A. Powell
Attorney, Agent, or Firm—Antonelli, Terry & Wands

[57] ABSTRACT

The present invention relates to a method of and apparatus for detecting the end point of plasma treatment. The method includes steps: selecting a plasma spectrum having a characteristic wavelength from the plasma spectrum occurring at the time of the plasma treatment reaction of a specimen; computing a secondary differential value of a function of the quantity of the plasma spectrum selected and the plasma treatment reaction time of the specimen; and detecting the end point of the plasma treatment reaction of the specimen by comparing the secondary differential value computed with preset reference values for judgment. The apparatus comprises a means of selecting plasma spectrum having a particular wavelength from the plasma spectrum occurring at the time of the plasma treatment reaction of the specimen, a means of converting the quantity of the plasma spectrum selected into an analog electric signal, a means of converting the analog electric signal into a value of digital data, a means of counting the plasma treatment reaction time of the specimen, a means of secondarily differentiating a function of the value of digital data and the plasma treatment reaction time, a means of making judgment by comparing the secondary differential value with preset reference values for judgment, and a means of giving an instruction for starting judgment to said means. Thus, accurate detection is achieved regardless of which curve is taken by the change in the reaction time of the quantity of plasma spectrum.

12 Claims, 5 Drawing Figures

METHOD OF AND APPARATUS FOR DETECTING AN END POINT OF PLASMA TREATMENT

BACKGROUND OF THE INVENTION

1. Field of the Invention:

The present invention relates to a method of and apparatus for detecting an end point of plasma treatment, and more particularly to a method of and apparatus for detecting an end point of plasma treatment which is suitable for detecting the end point of the reaction of plasma treatment of a specimen such as the substrate of a semiconductor device by selecting plasma spectrum having a characteristic wavelength from the plasma spectrum occurring at the time of reaction of plasma treatment of such a specimen and by making a judgment from the change of the quantity of the plasma light selected vis-à-vis the reaction time of the plasma treatment.

2. Description of the Prior Art:

As a method of detecting the end point of the reaction of plasma treatment of a specimen such as a semiconductor device substrate by selecting plasma spectrum having a characteristic wavelength from the plasma spectrum occurring at the time of the reaction and by detecting the same from the change of the quantity of the plasma spectrum selected vis-à-vis the reaction time of the plasma treatment, there is known, for example, one which is disclosed in Japanese Patent Laid-Open No. 115536/1981. This method is described hereinafter with reference to FIG. 1.

In FIG. 1, a curve 'a' indicates the intensity of radiation corresponding to a reaction product. In other words, the radiation corresponding to the reaction product increases sharply on starting the reaction, reaches its normal state within a brief period of time, decreases sharply on the end of the reaction, and then assumes its normal state. In this case, the end point of the plasma treatment reaction is detected at the point of time when the quantity of radiation corresponding to the reaction product, i.e., the quantity of plasma spectrum, has decreased sharply following the reaction's end and has assumed its normal state, namely, at the point of time when the differential value 'b' of a function of the quantity of plasma spectrum/reaction time has reached a predetermined level 1.

According to such a method, it is possible to detect the end point of the reaction of plasma treatment with good accuracy in a case where a curve of change in the reaction time of the quantity of plasma spectrum is similar to the one described above. However, in a case where the curve of change in the reaction time of the quantity of plasma spectrum fails to become similar to the one described above, and in a case where the magnitude of the level is large, there is a possibility that the differential value of a function of the quantity of spectrum/reaction time during the course of plasma treatment may reach the predetermined level, with the result that the end point of plasma treatment is detected by mistake in the course of plasma treatment. If the curve of change in the reaction time of plasma spectrum fails to become like the one described above, and if the magnitude of the level is, to the contrary, small, there is a possibility that the differential value of a function of the quantity of plasma spectrum/reaction time may fail to reach the predetermined level, with the result that it becomes impossible to detect the end point of the reaction of the plasma treatment. Thus, in a case where the curve of change in the reaction time of the quantity of plasma spectrum fails to show a curve as the one described above, there has been a drawback in attempts to detect with satisfactory accuracy the end point of the reaction of plasma treatment.

SUMMARY OF THE INVENTION

An object of the present invention is to provide a method of and an apparatus for detecting the end point of a plasma treatment which make it possible to detect with good accuracy the end point of the plasma treatment reaction of a specimen whatever curve may be taken by the change in the reaction time of the quantity of plasma spectrum.

The present invention is characterized in that, by using an apparatus comprising a means of selecting plasma spectrum having a characteristic wavelength from the plasma spectrum occurring at the time of the reaction of plasma treatment of a specimen, a means of converting the quantity of plasma spectrum selected to an analog electric signal, a means of converting the analog electric signal to a value of digital data, a means of counting the reaction time of the plasma treatment, a means of secondarily differentiating a function of the value of digital data and the counted reaction time of the plasma treatment, a means of making judgment by comparing the secondary differential value with preset reference values for judgment, and a means of giving an instruction for starting judgment to the said means, the end point of the reaction of the plasma treatment of the specimen is effected by selecting plasma spectrum having a characteristic wavelength from the plasma spectrum occurring at the time of the plasma treatment reaction of the specimen by computing the secondary differential value of a function of the quantity of plasma spectrum and the reaction time of the plasma treatment, and by making judgment by comparing the secondary differential value with the preset reference values for judgment, thereby making it possible to detect with good accuracy the end point of the reaction of plasma treatment of the specimen whatever curve may be taken by the change in the reaction time of the quantity of plasma spectrum.

DESCRIPTION OF THE PREFERRED EMBODIMENTS

A first embodiment of the present invention will be described with reference to FIGS. 2 to 4.

Figure 2:
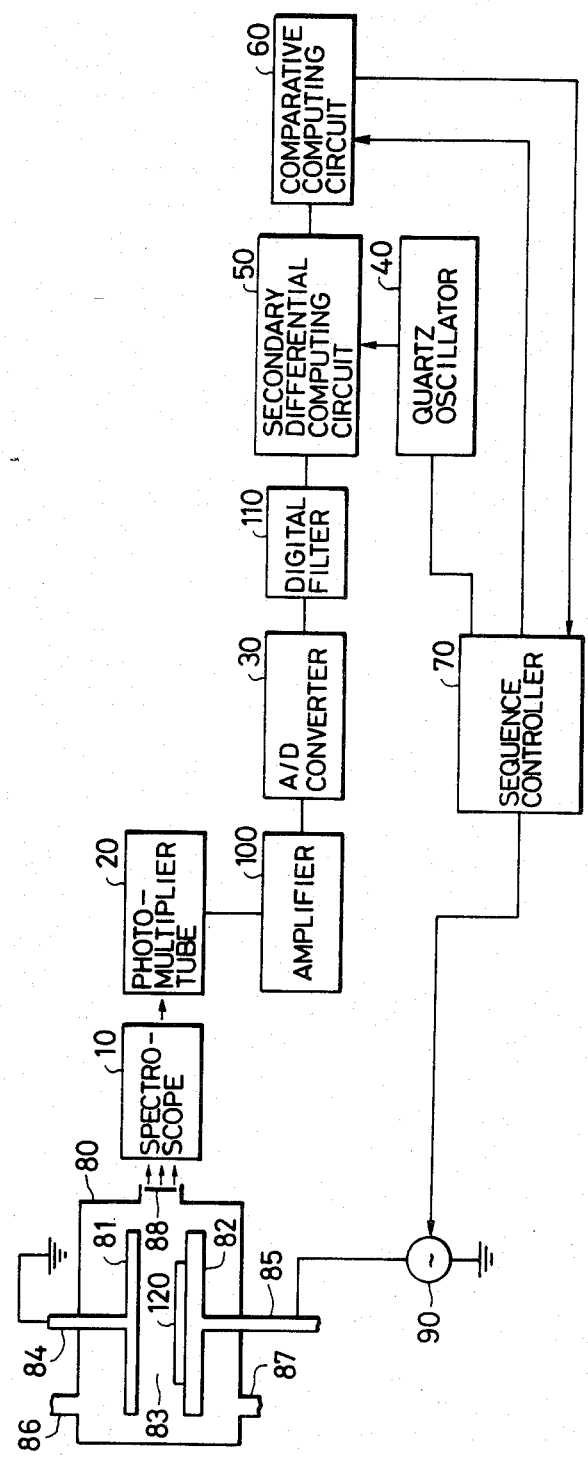
FIG. 2 is a block diagram illustrating a first embodiment of the apparatus for detecting the end point of plasma treatment according to the present invention.

In FIG. 2, the apparatus for detecting the end point of plasma treatment has the following: a means of selecting plasma spectrum with a characteristic wavelength from the plasma spectrum occurring at the time of the reaction of plasma treatment of a specimen, e.g., a spectroscope 10; a means of converting the quantity of the plasma spectrum selected to an analog electric signal, e.g., a photomultiplier tube 20; a means of converting the analog electric signal to a value of digital data, e.g., an A/D converter 30; a means of counting the reaction time of the plasma treatment of the specimen, e.g., a quartz oscillator 40; a means of secondarily differentiating between the function of the value of digital data and the plasma reaction time counted, e.g., a secondary differential computing circuit 50; a means of making judgment by comparing the secondary differential value with predetermined reference values for judgment, e.g., a comparative computing circuit 60; and a means of giving an instruction for starting judgment to the comparative computing circuit 60, e.g., a sequence controller 70.

For instance, in FIG. 2, in a treatment chamber 80 of the plasma etching apparatus, an opposing electrode 81 and a specimen electrode 82 are disposed in opposed relation to each other with a discharge space 83 therebetween. In other words, the opposing electrode 81 is disposed substantially horizontally at the lower end of an electrode shaft 84 provided at the top wall of the treatment chamber 80 with its lower end portion projecting inside the treatment chamber 80. Meanwhile, the specimen electrode 82 is disposed substantially horizontally at the upper end of an electrode shaft 85 provided at the bottom wall of the treatment wall 80 with its upper portion projecting into the treatment chamber 80, the specimen-mounting surface thereof facing upward. A nozzle 86 for introducing a reaction gas is provided at the top wall of the treatment chamber 80. A reaction gas-introducing system (not shown) is connected to the nozzle 86. An exhaust nozzle 87 is provided at the bottom wall of the treatment chamber 80. A vacuum exhausting unit (not shown) is connected to the nozzle 87. The electrode shaft 84 is grounded. The electrode shaft 85 is connected to a radio-frequency power supply 90, which serves as the power supply for the apparatus, and the radio-frequency power supply 90 is grounded.

In FIG. 2, a peep hole 88 is provided at the side wall corresponding to the discharge space 83 of the treatment chamber 80. The spectroscope 10 is disposed outside the treatment chamber 80 in correspondence with the peep hole 88. The photomultiplier tube 20 is connected to the spectroscope 10. In this arrangement, the A/D converter 30 is connected to the photomultiplier tube 20 via an amplifier 100. The secondary differential computing circuit 50 is connected to the A/D converter 30 via a digital filter 110. The quartz oscillator 40 and the comparative computing circuit 60 are connected to the secondary differential computing circuit 50. In addition, the quartz oscillator 40 and the comparative computing circuit 60 are connected to the sequence controller 70. In this arrangement, the sequence controller 70, which is connected to the radio-frequency power supply 90, has the function of issuing signals for starting and stopping discharge to the radio-frequency power supply 90. Furthermore, in this arrangement, positive and negative reference values have been preset in the comparative computing circuit 60 as reference values for judgment.

In FIG. 2, in this arrangement, one piece of specimen 120 is carried into the treatment chamber 80 by a known carrying means (not shown), and is mounted on the specimen-mounting surface of the specimen electrode 82 with the surface which will be treated facing upward. Subsequently, the pressure inside the treatment chamber 80 is reduced to a predetermined pressure setting by exhausting the air by means of the operation of the vacuum exhausting unit. Then, a reaction gas is introduced at a predetermined flow rate into the treatment chamber 80 via the nozzle 86. At the same time, part of the reaction gas so introduced is exhausted outside the treatment chamber 80 via the nozzle 87. In this way, the pressure inside the treatment chamber 80 can be adjusted to a predetermined etching pressure. In this state, a discharge starting signal is issued by the sequence controller 70 to the radio-frequency power supply 90, and predetermined radio-frequency power is applied to the specimen electrode 82 by the radio-frequency power supply 90 via the electrode shaft 85. Consequently, a flow discharge takes place between the opposing electrode 81 and the specimen electrode 82, i.e., in the discharge space 83. The reaction gas is made into plasma by this flow discharge, and the surface of the specimen 120 to be treated is etched by the plasma. At this time, plasma spectrum occurs, and plasma spectrum having a characteristic wavelength in this plasma spectrum is selected by the spectroscope 10 via the peep hole 88. The quantity of plasma spectrum selected by the spectroscope 10 is converted into an analog electric signal by the photomultiplier tube 20, and this analog electric signal is then amplified by the amplifier 100. The amplified analog electric signal is converted into a value of digital data by means of the A/D converter, and this value of digital data is made flat by the digital filter 110 and inputted into the secondary differential computing circuit 50. Meanwhile, at the point of time when a discharge-starting signal is issued by the sequencer 70 to the radio-frequency power supply 90, the counting of the etching reaction time, which is the reaction time of plasma reaction, begins at the quartz oscillator 40, and this etching reaction time thus counted is inputted into the secondary differential computing circuit 50 by the quartz oscillation 40. A secondary differential value of the function between the flattened value of digital data and the plasma etching reaction time counted is computed at the secondary differential computing circuit 50. The secondary differential value computed is inputted into the comparative computing circuit 60 by the secondary differential computing circuit 50. At the point of time when a predetermined time has elapsed after the starting of the plasma etching reaction of the specimen 120, an instruction signal for starting judgment is issued to the comparative computing circuit 60 by the sequence controller 70. Consequently, judgment is made at the comparative computing circuit 60 as comparison is made between the secondary differential value inputted by the secondary differential computing circuit 50 and the predetermined reference values for judgment. Subsequently, at the point of time when the secondary differential value has reached a predetermined reference value for judgment, the end point of the plasma etching reaction of the specimen 120 is detected. Furthermore, at this juncture, an end point judgment signal is issued by the comparative computing circuit 60 to the sequence controller 70, and, in turn, a discharge stop signal is issued to the radio-frequency power supply 90 by the sequence controller 70. Consequently, the flow discharge in the discharge space 83 is stopped. Subsequently, the specimen 120 is removed from the specimen electrode 82 by means of a known carrying means, and is carried outside the treatment chamber 80.

Figure 3:
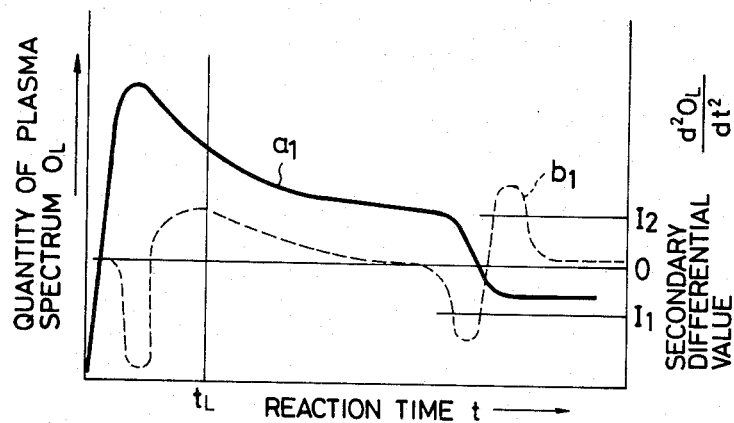
FIGS. 3 and 4 are diagrams illustrating relationships among the quantity of plasma spectrum, the secondary differential value of a function of the quantity of plasma spectrum/reaction time, and the reaction time.

In FIG. 3, the reference character $a_1$ denotes a curve of change in the reaction time of plasma spectrum having a characteristic wavelength and selected from the plasma spectrum corresponding to the reaction product produced at the time of the plasma etching reaction of the specimen. The quantity of plasma spectrum ($O_L$) in this case increases sharply on starting the plasma etching reaction, shows a gradual declining trend until a point close to the end of the reaction, declines sharply upon the end of the reaction, and then assumes its normal state. Such a change curve of the reaction time of plasma spectrum appears, for example, when a specimen undergoes plasma etching after the treatment chamber coated with a material containing carbon on its inner surface has been subjected to plasma cleaning by a radio-frequency discharge using an oxygen gas. The reference character $b_1$ shows a curve of the secondary differential value of a function of the quantity of plasma spectrum/reaction time.

In FIG. 3, at the point when the time $t_L$ has elapsed during which the quantity of plasma spectrum shows a gradual rate of change after the starting of the plasma etching reaction of the specimen, an instruction signal for starting judgment is issued by the sequencer to the comparative computing circuit. As a result, an operation begins for making judgment by comparison of the secondary differential value ($d^2O_L/dt^2$) with preset reference values for judgment. Then, at the point of time when the secondary differential value has first reached a negative reference value ($I_1$) for judgment among the preset reference values, the plasma etching reaction of the specimen approaches its end point. In other words, judgment is made of the trend which occurs when the quantity of plasma spectrum begins to decrease. Subsequently, at the point of time when the secondary differential value has reached a positive reference value ($I_2$) among the preset reference values for judgment, judgment is made of the end point of the plasma etching reaction of the specimen.

Figure 1:
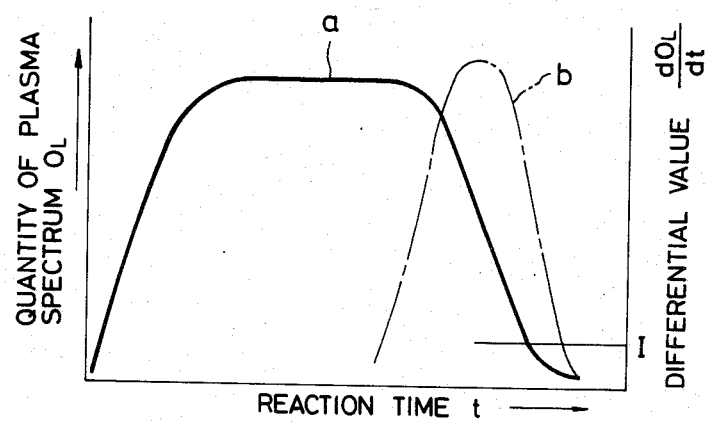
FIG. 1 is a diagram illustrating the relationships among the quantity of plasma spectrum, the differential value of a function of the quantity of spectrum/reaction time, and the reaction time, which serves to explain a conventional method of detecting the end point of plasma treatment.

Incidentally, even in a case where the curve of change in the reaction time of the quantity of plasma spectrum is a curve as shown in FIG. 1, the end point of the plasma etching reaction of the specimen can be detected, as described above.

Figure 4:
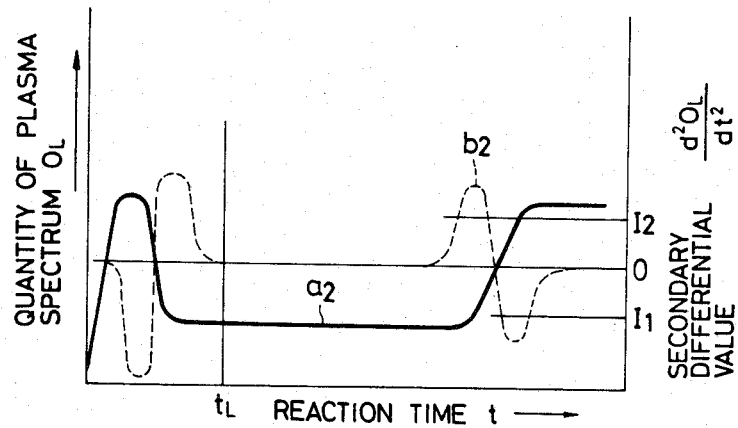

Referring to FIG. 4, the reference character $a_2$ shows a curve of change in the reaction time of the quantity of plasma spectrum having a characteristic wavelength and selected from the plasma spectrum corresponding to the condition of the reaction gas and the quantity of the nuclide of a radical occurring at the time of the plasma etching reaction of the specimen. The quantity of plasma spectrum ($O_L$) in this case increases sharply on starting the reaction of plasma etching, and then it decreases sharply and assumes its normal state. Subsequently, it increases sharply upon the completion of the reaction, and then assumes its normal state. The reference character $b_2$ indicates a curve of the secondary differential value of a function of the quantity of plasma spectrum/reaction time in this case.

In FIG. 4, at the point when the quantity of plasma spectrum becomes a fixed quantity has elapsed after elapse of the time $t_L$ from the starting of the plasma etching reaction of the specimen, an instruction signal for starting judgment is issued by the sequencer to the comparative computing circuit. As a result, an operation begins for making judgment by comparison of the secondary differential value ($d^2O_L/dt^2$) with preset reference values. Then, the plasma etching reaction of the specimen approaches its end at a point of time when the secondary differential value has first reached a positive reference value ($I_1$) among the preset reference values for judgment. In other words, judgment is made of the trend which occurs when the quantity of plasma spectrum begins to increase. Subsequently, at the point of time when the secondary differential value has reached a negative reference value ($I_2$) among the preset reference values for judgment, judgment is made of the end point of the plasma etching reaction of the specimen.

According to this embodiment, at the point of elapse of time when the quantity of plasma spectrum shows a gradual rate of change as well as a fixed quantity, an operation is started for making judgment by comparison of the secondary differential value of a function of the quantity of plasma spectrum/reaction time with preset reference values. Furthermore, after this secondary differential value has reached either of the preset reference and negative reference values for judgment, and at the point of time when this secondary differential value has reached the remaining reference value for judgment, the end point of the plasma etching reaction of the specimen can be detected. As a result, it is possible to detect with satisfactory accuracy the end point of plasma etching reaction whatever curve may be taken by the change in the reaction time of the quantity of plasma spectrum.

Incidentally, in a case where it is necessary to terminate the etching by causing the material which is being etched to remain on the substrate material constituting the specimen, at the point of time when the secondary differential value of a function of the quantity of plasma spectrum/reaction time has first reached either of the preset positive and negative reference values for judgment, judgment can be effected by causing the comparative computing circuit to issue a termination judging signal to the sequencer and by causing the sequencer to issue a discharge stopping signal to the radio-frequency power supply.

Figure 5:
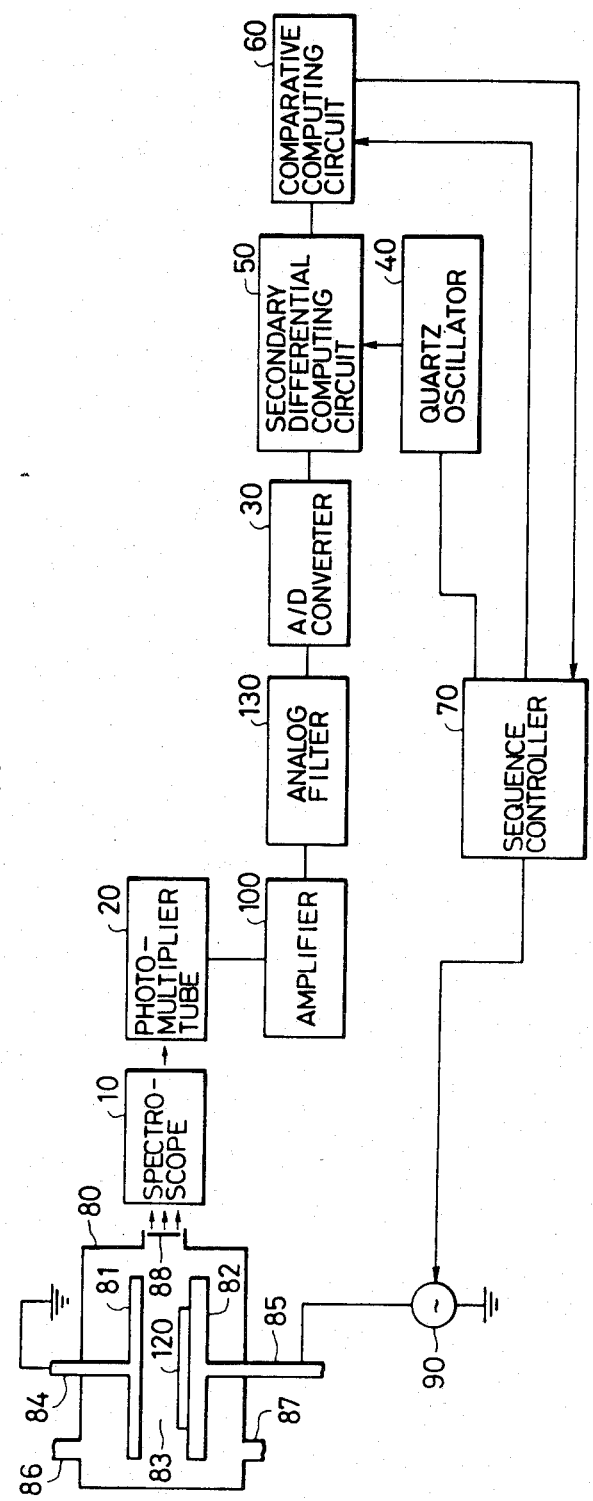
FIG. 5 is a block diagram showing a second embodiment of the apparatus for detecting the end point of plasma treatment according to the present invention.

FIG. 5 shows a second embodiment of the present invention. The points that differ from FIG. 2 which shows the first embodiment are that an A/D converter 30, which is a means of converting an analog electric signal to a value of digital data, is connected to the photomultiplier tube 20, which is a means of converting the quantity of plasma spectrum into the analog electric signal via the amplifier 100 and the analog filter 130, and that a secondary differential computing circuit 50, which is a means of secondarily differentiating the function of the value of digital data and the counted reaction time of plasma treatment, is connected to the A/D converter 30. In FIG. 5, those means that are the same as those shown in FIG. 2 are indicated by the same reference characters, and description of them will be omitted.

According to the second embodiment, it is possible to obtain effects similar to those of the first embodiment.

As explained above, the present invention is characterized in that, by using an apparatus comprising a means of selecting plasma spectrum having a characteristic wavelength from the plasma spectrum occurring at the time of the reaction of plasma treatment of a specimen, a means of converting the quantity of plasma spectrum selected to an analog electric signal, a means of converting the analog electric signal to a value of digital data, a means of counting the reaction time of the plasma treatment, a means of secondarily differentiating a function of the value of digital data and the counted reaction time of the plasma treatment, a means of making judgment by comparing the secondary differential value with preset reference values for judgment, and a means of giving an instruction for starting judgment to said means, the end point of the reaction of the plasma reaction of the specimen is effected by selecting plasma spectrum having a characteristic wavelength from the plasma spectrum occurring at the time of the plasma treatment reaction of the specimen by computing a secondary differential value of the function of the quantity of plasma spectrum and the reaction time of the plasma treatment, and by making judgment by comparison of the secondary differential value with the preset reference values for judgment. Consequently, the present invention achieves an effect whereby it is possible to detect with satisfactory accuracy the end point of the plasma treatment reaction of the specimen whatever curve may be taken by the change in the reaction time of the quantity of plasma spectrum.

What is claimed is:

1. A method of detecting the end point of plasma treatment comprising a step of selecting plasma spectrum having a characteristic wavelength from the plasma spectrum occurring at the time of reaction of the plasma treatment of a specimen, a step of computing a secondary differential value of a function of the quantity of said plasma spectrum selected and the plasma treatment reaction time of said specimen, and a step of detecting the end point of the plasma treatment reaction of said specimen by comparing said computed secondary differential value with preset reference values for judgment.

2. A method of detecting the end point of plasma treatment according to claim 1, wherein an operation for making judgment by comparing said secondary differential value with said reference values for judgment is started at the point when the time has elapsed during which the quantity of said plasma spectrum shows a gradual rate of change.

3. A method of detecting the end point of plasma treatment according to claim 1, wherein an operation for making judgment by comparing said secondary differential value with said reference values for judgment is started at the point of time when the quantity of said plasma spectrum becomes a fixed quantity.

4. A method of detecting the end point of plasma treatment according to claim 1, wherein said reference values for judgment are positive and negative reference values for judgment, and the end point of the reaction of plasma etching of said specimen is detected at the point of time when said secondary differential value has reached both of said positive and negative reference values for judgment.

5. A method of detecting the end point of plasma treatment according to claim 1, wherein said reference values for judgment are positive and negative reference values for judgment, and the end point of the plasma treatment reaction is detected at the point of time when said secondary differential value for judgment has first reached either of said positive and negative reference values for judgment.

6. A method of detecting the end point of plasma treatment according to claim 1, wherein said secondary differential value is computed by converting the quantity of said plasma spectrum into an analog electric signal, by converting said analog electric signal into a value of digital data, and by secondarily differentiating a function of said value of digital data and the plasma treatment reaction time of said sample.

7. A method of detecting the end point of plasma treatment according to claim 6, wherein said analog electric signal is amplified, and said value of digital data is flattened.

8. A method of detecting the end point of plasma treatment according to claim 6, wherein said analog electric signal is amplified and flattened, and said analog electric signal is converted into said value of digital data.

9. An apparatus for detecting the end point of plasma treatment comprising a means of selecting plasma spectrum having a characteristic wavelength from the plasma spectrum occurring at the time of the plasma treatment reaction of a specimen, a means of converting the quantity of said selected plasma spectrum into an analog electric signal, a means of converting said analog electric signal into a value of digital data, a means of counting the plasma treatment reaction time of said specimen, a means of secondarily differentiating a function of said value of digital data and said plasma treatment reaction time, a means of making judgment by comparing said secondary differential value with preset reference values for judgment, and a means of giving an instruction for starting judgment to said means.

10. An apparatus for detecting the end point of plasma treatment according to claim 9, wherein a positive and negative reference value for judgment are provided as said reference values for judgment to said means of making judgment by comparing said secondary differential value with preset reference values for judgment.

11. An apparatus for detecting the end point of plasma treatment according to claim 9, wherein said means of converting said analog electric signal into a value of digital data is connected to said means of converting the quantity of said plasma light into an analog electric signal via an amplifier, and said means of secondarily differentiating a function of said value of digital data and said plasma treatment reaction time is connected to said means of converting said analog electric signal into a value of digital data via a digital filter.

12. An apparatus for detecting the end point of plasma treatment according to claim 9, wherein said means of converting said analog electric signal into a value of digital data is connected to said means of converting the quantity of said plasma light into an analog electric signal via an amplifier and an analog filter.

* * * * *